United States Patent [19]

Senter et al.

[11] Patent Number: 5,306,307
[45] Date of Patent: Apr. 26, 1994

[54] SPINAL DISK IMPLANT

[75] Inventors: Howard J. Senter, Pittsburgh, Pa.; William R. Wagner; Richard L. Lariviere, both of Escondido, Calif.

[73] Assignee: Calcitek, Inc., Carlsbad, Calif.

[21] Appl. No.: 733,710

[22] Filed: Jul. 22, 1991

[51] Int. Cl.⁵ .......................... A61F 2/44; A61F 2/02
[52] U.S. Cl. ........................................ 623/17; 623/11
[58] Field of Search ................................ 623/17, 11

[56] References Cited

U.S. PATENT DOCUMENTS

| | | |
|---|---|---|
| 2,677,369 | 5/1954 | Knowles . |
| 3,848,601 | 11/1974 | Ma et al. . |
| 3,867,728 | 2/1975 | Stubstad et al. ............. 623/17 |
| 4,309,777 | 1/1982 | Patil . |
| 4,349,921 | 9/1982 | Kuntz . |
| 4,714,469 | 12/1987 | Kenna . |
| 4,743,256 | 5/1988 | Brantigan . |
| 4,759,766 | 7/1988 | Buether-Janz et al. ...... 623/17 |
| 4,759,769 | 7/1988 | Hedman et al. . |
| 4,772,287 | 9/1988 | Ray et al. . |
| 4,834,757 | 5/1989 | Brantigan ................... 623/17 |
| 4,863,476 | 9/1989 | Shappard . |
| 4,863,477 | 9/1989 | Monson ...................... 623/17 |
| 4,874,389 | 10/1989 | Downey . |
| 4,904,260 | 2/1990 | Ray et al. . |
| 4,904,261 | 2/1990 | Dove et al. . |
| 4,911,718 | 3/1990 | Lee et al. .................... 623/17 |
| 4,917,704 | 4/1990 | Frey et al. ................... 623/17 |
| 4,932,969 | 6/1990 | Frey et al. ................... 623/17 |
| 4,932,975 | 6/1990 | Main et al. . |
| 4,936,848 | 6/1990 | Bagby . |
| 4,946,378 | 8/1990 | Hirayama et al. . |
| 4,955,908 | 9/1990 | Frey et al. . |
| 4,997,432 | 5/1991 | Keller . |
| 5,002,576 | 5/1991 | Fuhrman et al. . |
| 5,015,247 | 5/1991 | Michelson . |
| 5,071,437 | 12/1991 | Steffee ........................ 623/17 |

FOREIGN PATENT DOCUMENTS

| | | |
|---|---|---|
| 0042271 | 12/1981 | European Pat. Off. ...... 623/17 |
| 0317972 | 5/1989 | European Pat. Off. ...... 623/17 |
| 0346269 | 12/1989 | European Pat. Off. ...... 623/17 |
| 0453393 | 10/1991 | European Pat. Off. ...... 623/17 |
| 3002298 | 7/1981 | Fed. Rep. of Germany ...... 623/17 |
| 9000037 | 1/1990 | World Int. Prop. O. ...... 623/17 |
| 9105521 | 5/1991 | World Int. Prop. O. ...... 623/17 |

OTHER PUBLICATIONS

T. Koyama et al., "Porous Hydroxyapatite Ceramics for Use in Neurosurgical Practice", *Surg. Neurol.*, vol. 25, pp. 71-73 (1986).

(List continued on next page.)

*Primary Examiner*—Randall L. Green
*Assistant Examiner*—Elizabeth M. Burke
*Attorney, Agent, or Firm*—Gregory Garmong; Donald R. Greene; Saul Leitner

[57] ABSTRACT

A spinal disk implant is implanted between vertebrae of the human spine following discectomy. The implant comprises a solid body having four sides and a pair of spaced-apart, opposed bases. The four sides include spaced-apart, opposed anterior and posterior faces, and a pair of spaced-apart, opposed transverse faces. Each transverse face has an anterior platform adjacent to the anterior face. The anterior platform is spaced apart from the opposed anterior platform by a maximum anterior platform spacing. A posterior ledge is oriented at an insertion angle relative to an opposed posterior ledge of the opposed transverse face. At least one of the posterior ledges has a pattern of serrations. There is a ridge on at least one of the transverse faces, positioned between the anterior platform and the posterior ledge and extending in the direction perpendicular to the bases. The top of the ridge is spaced apart from the opposed transverse face by an amount greater than the anterior platform spacing. The implant is desirably formed at least in part from a material that bonds with natural bone after implant, such as the ceramic hydroxylapatite.

24 Claims, 5 Drawing Sheets

OTHER PUBLICATIONS

Stephen D. Cook et al., "Evaluation of Hydroxylapatite Graft Materials in Canine Cervical Spine Fusions", *Spine,* vol. 11, No. 4, pp. 305–309 (1986).

Howard Senter et al., "Anterior Cervical Discectomy with Hydroxylapatite Fusion", *Neurosurgery,* vol. 25, No. 1, pp. 39–43 (1989).

G. Lozes et al., "Discectomies of the Lower Cervical Spine Using Interbody Biopolymer (B.O.P.) Implants", *Acta Neurochirurgica,* vol. 96, pp. 88–93 (1989).

M. Jarcho, "Calcium Phosphate Ceramics as Hard Tissue PRosthetics", *Clinical Orthopaedics,* vol. 157, pp. 259–278 (1981).

M. Jarcho, "Biomaterial Aspects of Calcium Phosphates", *Dental Clinics of North America,* vol. 30, No. 1, pp. 25–47 (1986).

M. Block, "Evaluation of Hydroxylapatite–Coated Titanium Dental Implants in Dogs", *J. Oral Maxillofac. Surg.,* vol. 45, pp. 601–607 (1987).

Stephen D. Cook et al., "Interface Mechanics and Histology of Titanium and Hydroxylapatite–Coated Titanium for Dental Implant Applications", *International Journal of Oral & Maxillofacial Implants,* vol. 2, No. 1, pp. 15–22 (1987).

Stephen D. Cook et al., "Hydroxylapatite–Coated Titanium for Orthopedic Implant Applications", *Clinical Orthopedics and Related Research,* No. 232, pp. 225–243 (1988).

T. Yamamuro et al., "Replacement of the Lumbar Vertebrae of Sheep with Ceramic Prostheses", *The Journal of Bone and Joint Surgery,* vol. 72-B, pp. 889–893 (1990).

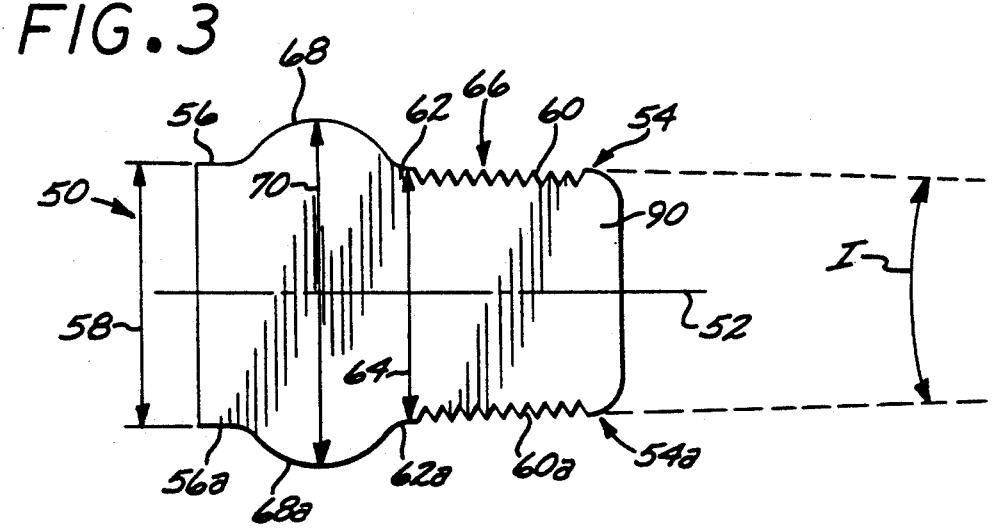
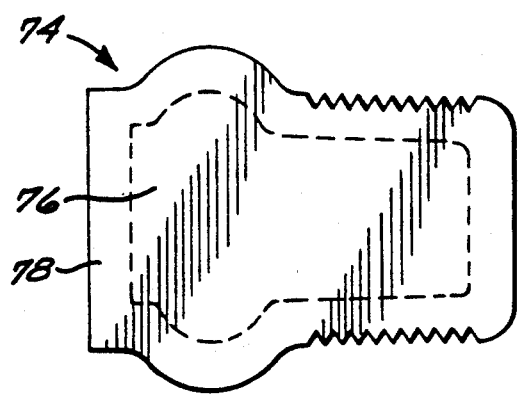
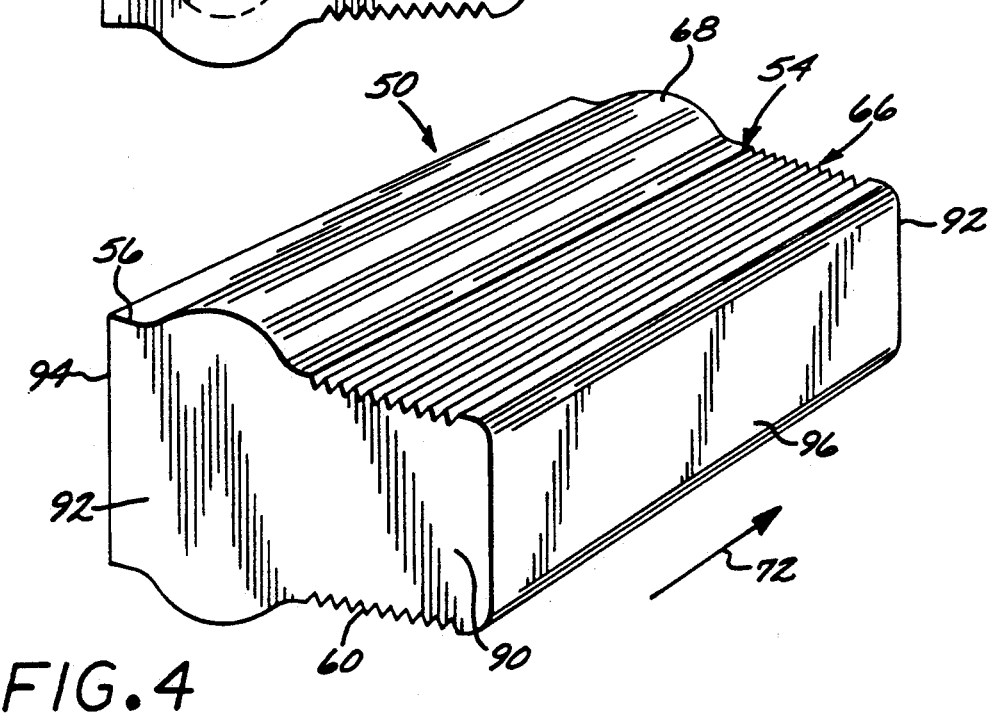

SPINAL DISK IMPLANT

BACKGROUND OF THE INVENTION

This invention relates to implants surgically placed into the human body, and, more particularly, to an implant placed between two vertebrae to fuse them together.

The human spine is composed of a column of 33 bones, termed vertebrae, and their joining structures. The 24 vertebrae nearest the head, collectively termed the presacral vertebrae, are separate bones capable of individual movement. The bodies of the presacral vertebrae are generally connected by anterior and posterior longitudinal ligaments and by discs of fibrocartilage, termed intervertebral disks, positioned between opposing faces of adjacent vertebral bodies. These mobile vertebrae may be classified by their position and function into either cervical, thoracic, or lumbar vertebrae. The remaining 9 vertebrae are fused to form the sacrum (5 vertebrae) and the coccyx (4 vertebrae) and are incapable of individual movement. This column of vertebrae and intervertebral disks form a central axis for supporting the load of the head and torso. The vertebral body and the dorsal vertebral arch of each of the 24 mobile presacral vertebrae enclose an opening, termed the vertebral foramen, through which the spinal cord, a column of nerve tissue which communicates nerve impulses between the brain and the rest of the body, and the spinal nerve roots pass and are protected from damage.

The presacral vertebrae are normally held in a precise relation to each other by the intervertebral disks, the longitudinal ligaments, and the musculature of the body. These vertebrae can move relative to adjacent vertebrae in various manners, permitting the head to be turned relative to the body and providing a wide range of flexibility to the spine. The movement between individual pairs of vertebrae is limited to prevent local pressure on the spinal cord or excessive bending of the spinal cord. Such pressure or bending could possibly result in disorders associated with blockage of the nerve impulses traveling along the spinal cord, in turn producing pain, paresthesia, or loss of motor control which must be resolved by removing the causative condition.

The nerve conduction disorders may also be associated with the intervertebral disks or the bones themselves. One such condition is a herniation of the intervertebral disk, in which a small amount of tissue protrudes from the sides of the disk into the foramen to compress the spinal cord. A second common condition involves the development of small bone spurs, termed osteophytes, along the posterior surface of the vertebral body, again impinging on the spinal cord.

Upon identification of the abnormality causing the conduction disorders, surgery may be required to correct the problem if more conservative treatment fails. For those problems associated with the formation of osteophytes or herniations of the intervertebral disk, one such surgical procedure is intervertebral discectomy. In this procedure, the involved vertebral bodies are exposed and the intervertebral disk is removed, thus removing the offending tissue, or providing access for the removal of the bone osteophytes. A second procedure, termed a spinal fusion, may then be required to fix the vertebral bodies together to prevent movement and maintain the space originally occupied by the intervertebral disk. Although there may result some minor loss of flexibility in the spine, because of the large number of vertebrae the loss of mobility is usually acceptable.

During a spinal fusion following a discectomy, an implant is inserted into the intervertebral space. This intervertebral implant is often a bone graft removed from another portion of the patient's body, termed an autograft. The use of bone taken from the patient's body has the important advantage of avoiding rejection of the implant, but has some shortcomings. There is always a risk in opening a second surgical site for obtaining the implant, which can lead to infection or pain for the patient, and the site of the implant is weakened by the removal of bony material. The bone implant may not be perfectly shaped and placed, leading to slippage or absorption of the implant, or failure of the implant to fuse with the vertebrae.

Other options for a graft source for the implant are bone removed from cadavers, termed an allograft, or from another species, termed a xenograft. In these cases, while there is the benefit of not having a second surgical site as a possible source of infection or pain, there is the increased difficulty with graft rejection and the risk of transmitting communicable diseases.

An alternative approach to using a bone graft is to use a manufactured implant made of a synthetic material that is biologically compatible with the body and the vertebrae. Several compositions and geometries of such implants have been utilized, ranging from simple blocks of material to carefully shaped implants, with varying success. No fully satisfactory implant has been reported. In some instances, the implanting surgery is readily accomplished, but the results are unsatisfactory due to side effects or dislocation of the implant. In other instances, the implant requires a complex surgical procedure that is difficult to perform and still may not lead to correction of the problem for the reasons indicated.

There is therefore a need for an improved spinal disk implant, which is both readily utilized in a surgical procedure and has a high probability of success without undesirable side effects. The present invention fulfills this need, and further provides related advantages.

SUMMARY OF THE INVENTION

The present invention provides a surgical implant, and its method of use, that is implanted between two vertebrae during a procedure in which the two vertebrae are fused together. The surgical disk implant is readily manufactured of biologically compatible materials in the required shape and with preselected dimensions, so that a properly dimensioned implant is available for the particular vertebrae being fused together. The disk implant of the invention may be readily implanted by established surgical procedures, with minimal chances of surgical difficulty. The geometry of the implant ensures good load bearing and support through the fused vertebrae, and minimizes the likelihood of the implant dislocating relative to the vertebrae either during surgery or during the post-operative fusing process.

In accordance with the invention, a spinal disk implant comprises a solid body having four sides and a pair of spaced-apart, opposed bases. The four sides include spaced-apart, opposed anterior and posterior faces, and a pair of spaced-apart, opposed transverse faces. Each transverse face has an anterior platform adjacent to the anterior face. The anterior platform is spaced apart from the opposed anterior platform by a maximum anterior platform spacing. A posterior ledge is oriented at an insertion angle relative to an opposed posterior ledge of the opposed transverse face. At least one of the posterior ledges has thereon a pattern of serrations. There is a ridge on at least one of the transverse faces, positioned between the anterior platform and the posterior ledge and extending in the direction perpendicular to the bases. The top of the ridge is spaced apart from the opposed transverse face by an amount greater than the anterior platform spacing. There may be a ridge on one or both transverse faces.

The spinal disk implant is a generally rectangular block of material, which has three distinct regions. The anterior platform on each transverse face are preferably, but not necessarily, parallel to each other and spaced apart by the desired spacing of the vertebrae. The disk implant is surgically implanted so that the anterior cortical bone regions of the vertebrae contact the anterior platforms on the opposing transverse faces, precisely defining the final separation of the vertebrae. This separation is maintained after implantation to a good degree of accuracy, because the majority of the load carried by the vertical spinal column is reacted through the anterior cortical bone of the vertebrae and the anterior platform region of the surgical disk implant.

The posterior ledge is preferably, although not necessarily, tapered inwardly to permit the implant to be inserted between the vertebrae during the surgical procedure. The surface of the intermediate ridge is preferably smooth for the same reason. The serrations of the posterior ledge, acting together with the intermediate ridge, key the engagement of the implant with each vertebra and prevent dislocation of the implant with respect to the vertebrae. The principal keying engagement is with the cancellous bone region of the vertebrae. Preferably, a relatively small portion of the load borne by the spine is carried through the posterior ledge and the ridge, because their contact with the cancellous bone makes settling in of the implant into the vertebrae a greater concern in this region. The anterior platform and/or the posterior ledge and/or the ridge can be bowed outwardly slightly, to match the shape of the contacted vertebrae more precisely.

The spinal disk implant may alternatively be described in terms of the functional relations of its structural elements. In accordance with this aspect of the invention, a spinal disk implant is placed between two adjacent vertebrae previously originally having a spinal disk therebetween, each vertebra having an anterior cortical bone region and a central cancellous bone region. The disk implant comprises a solid body of substantially the same height as the natural spacing between the anterior cortical bone regions of the two adjacent vertebrae and of equal-to or lesser width than the spinal disk originally between the two vertebrae. The disk implant has means for supportively engaging the coritcal bone regions of the adjacent vertebrae, the means for supportively engaging including opposing, spaced apart anterior platforms, and means for achieving keying engagement of the implant with the cancellous bone region of each vertebra to prevent dislocation of the implant with respect to the two vertebrae after implantation of the implant between the two vertebrae.

The spinal disk implant is preferably made in whole or in part of a ceramic material such as (calcium) hydroxylapatite. Hydroxylapatite ("HA") has a composition and crystal structure similar to that of the mineral phase of natural bone, and has proven biocompatibility with natural bone. Alternatively, the spinal disk implant may be made in whole or in part of a biocompatible orthopedic polymer ("BOP"), or other suitable material. The implant may be made in its entirety of such materials, or may be made of a metal such as a titanium alloy, or a metal covered with a layer of the ceramic such as HA or BOP. Additionally, the spinal disk implant may be made with its surface microporous so that it may be impregnated with therapeutic agents prior to implantation. The implant may then function as a delivery vehicle for the impregnated therapeutic agents, such as antibiotics or bone stimulating factors such as bone morphogenic protein ("BMP") or osteogenin.

The present invention provides an advance in the art of intervertebral disk implants. The implant of the invention may be readily placed surgically, and is designed to provide load bearing capability to the spine while minimizing the likelihood of dislocation of the implant. Other features and advantages of the invention will be apparent from the following more detailed description of the preferred embodiments, taken in conjunction with the accompanying drawings which illustrate, by way of example, the principles of the invention.

BRIEF DESCRIPTION OF THE DRAWINGS

FIG. 3 is an elevational view of the spinal disk implant of the invention;

FIG. 4 is a perspective view of the spinal disk implant of FIG. 3;

FIG. 5 is another embodiment of the spinal disk implant;

FIG. 6 is a diagrammatic depiction of the surgical procedure for implanting the spinal disk implant of the invention, wherein

DETAILED DESCRIPTION OF THE PREFERRED EMBODIMENTS

Figure 1:
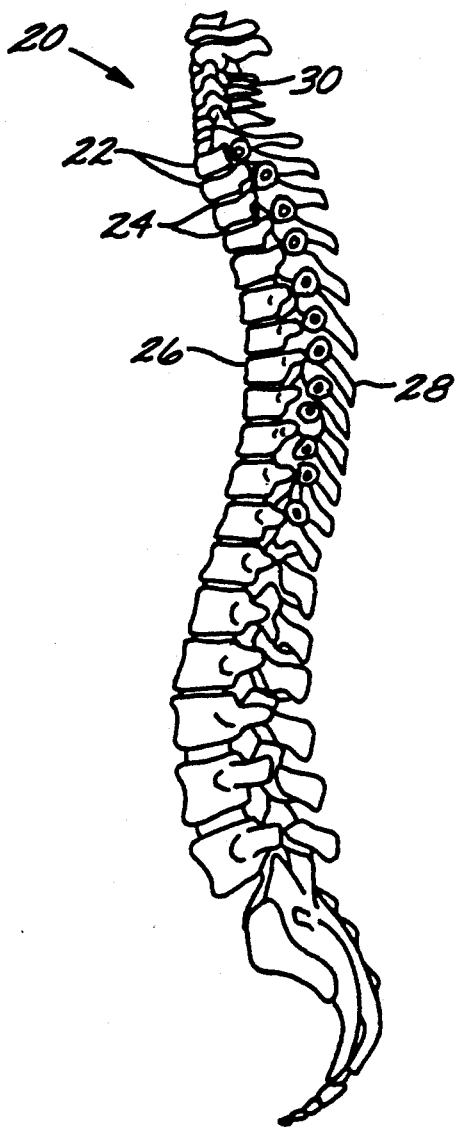
FIG. 1 is a side elevational view of the spine.

FIG. 1 depicts a human spine 20. The spine 20 is formed from thirty-three individual vertebrae 22, with the 24 uppermost vertebrae in most cases separated by intervertebral disks 24. The spine 20 is described as having an anterior side 26 and a posterior side 28.

Figure 2:
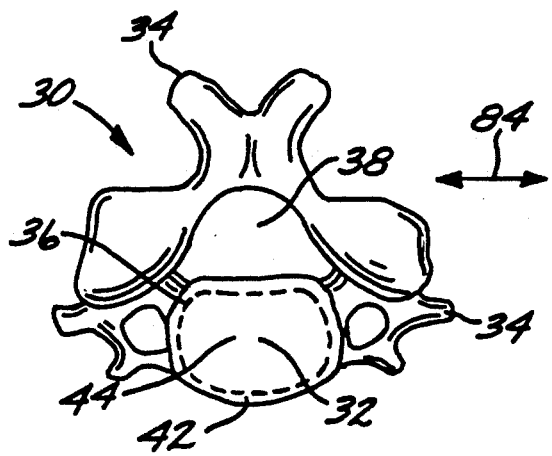
FIG. 2 is a plan view of a cervical vertebra.

FIG. 2 depicts one of the vertebrae, here one of the cervical vertebrae 30. (A cervical vertebra has been chosen for illustration, but the other vertebra are similar in relevant aspects and differ primarily in details of geometry.) The vertebra 30 includes a vertebral body region 32, and various processes 34. A cervical disk 36, indicated in phantom lines, overlies the vertebral body region 32 in the natural condition. A central opening through the vertebra 30 is the foramen 38, through which the spinal cord and the spinal nerve roots pass.

The vertebral body region 32 includes two distinct types of natural bone. A layer of cortical bone is found at an anterior edge 42 of the vertebral body region 32. The cortical bone is a hard, dense type of bone, having high strength. A central portion 44 of the vertebral body region 32 is made of cancellous bone, which is a more resilient, weaker, and less dense type of bone.

A spinal disk implant 50, shown in FIGS. 3 and 4, has a structure designed for implantation between the vertebral body regions of two adjacent vertebrae 22. This spinal disk implant 50 is readily inserted between the vertebrae during a surgical procedure, produces a load-bearing joint in which the majority of the load on the spine 20 is borne through the cortical bone, and is highly resistant to dislocation away from its proper position between the vertebrae.

The implant 50 is a right-angled prismatic body 90 having four sides and a pair of spaced-apart, opposed parallel bases 92. The four sides include spaced apart anterior and posterior faces 94 and 96, and a pair of spaced-apart, opposed transverse faces 54. In the elevational view of FIG. 3, the preferred embodiment of the implant 50 is seen to be bilaterally symmetric about a transverse central plane 52 positioned between the pair of opposing, spaced-apart transverse faces 54.

Each transverse face 54 includes three regions. An anterior platform 56 of each transverse face 54 is parallel (in the illustrated embodiment) to an opposing anterior platform 56a on an opposing transverse face 54a. The two anterior platforms 56 and 56a are separated by a preselected distance 58, which is substantially equal to the natural spacing between the two vertebrae between which the implant 50 is to be placed. This spacing criterion provides the basis for selecting appropriately sized implants 50.

A posterior ledge 60 is tapered inwardly, toward the central plane 52. The angular orientation between the two posterior ledges 60 and 60a is an insertion angle I. An end 62 of the posterior ledge 60 closest to the anterior platform 56 is spaced from a corresponding end 62a of the opposing posterior ledge 60a by a distance 64, which is preferably equal to or less than the distance 58. The angle I (between the two posterior ledges 60 and 60a) is from 0 degrees (no taper) to about 10 degrees, is preferably from about 0.5 to about 10 degrees, and is most preferably about 5.2+/−1 degrees. The implant is operable with no taper. However, testing has indicated that an insertion angle I of more than about 0.5 degrees imparts a slight wedge shape to the implant and significantly aids in achieving a smooth surgical insertion of the implant between the vertebrae. If the insertion angle is more than about 10 degrees, the geometry of the implant makes achieving full contact with the vertebrae difficult, and can interfere with satisfactory post-operative fusion.

A pattern of serrations 66, extending perpendicular to the plane of the illustration of FIG. 3 and thence in the direction perpendicular to the bases 92, is present on the posterior ledge 60. The serrations are desirably in the form of protrusions outwardly from the posterior ledge 60 extending across a portion of the surface. The serrations may be small teeth, continuous small ridges, bumps, or other equivalently performing structure. The serrations 66 interlock with the cancellous bone of the vertebrae to inhibit dislocation (movement) of the implant 50 relative to the vertebrae after implantation.

On the transverse face 54, positioned between the anterior platform 56 and the posterior ledge 60, is an intermediate ridge 68. The ridge 68 extends perpendicular to the plane of the illustration of FIG. 3 and thus perpendicular to the bases 92. The top of the ridge 68 is separated from the top of the ridge 68a on the opposing transverse face 54a by a distance 70. The distance 70 is greater than either the distance 58 or 64. The ridge 68 is preferably smooth, without serrations, to permit it to be surgically implanted in the manner to be described subsequently.

Dislocation (movement) of any spinal implant is a serious concern, and the present implant 50 is designed to avoid such movement. Dislocation of the implant 50 posteriorly toward the foramen 38 is of particular concern, because such dislocation could result in the implant 50 impinging against the spinal cord. The combination of the ridge 68, the serrations 66, and the slightly wedge-shaped configuration of the implant 50 all aid in avoiding dislocation of the implant 50, and particularly in avoiding dislocation in the direction of the spinal cord.

The implant may be interpreted as being formed by extending a planar section of the shape shown in FIG. 3 in the direction perpendicular to the bases 92, sometimes termed a prism generator 72. The result in the case of the preferred embodiment is a right prismatic body that is bilaterally symmetric about the transverse central plane 52, but other forms of the invention may not have the bilateral symmetry about the plane 52.

Figure 8:
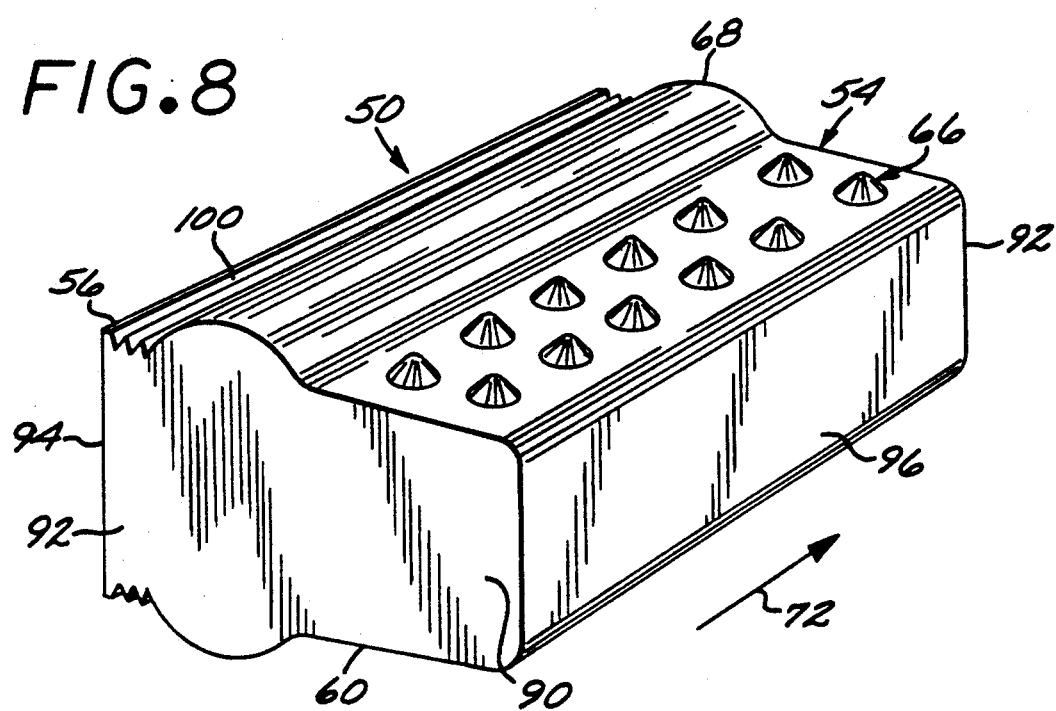
FIG. 8 is a perspective view similar to FIG. 4 of another embodiment of the invention.

In the embodiment of FIGS. 3-5, the structure of each transverse face 54 is a mirror image of the other, symmetric face 54a. Other embodiments of the implant need not be symmetric about a central plane, but can be asymmetric for use in particular procedures. FIG. 8 illustrates an asymmetric implant 50' having two asymmetric features. (Features corresponding to those of FIGS. 3-5 bear the same numbering.) There is only one ridge 68, and the pattern of serrations 66 is found on only one of the transverse faces 54. Also, in this case the serrations 66 are in the form of dimples rather than the form shown in FIGS. 3-5. These asymmetries need not be used together, and, for example, an operable implant may have only one ridge but serrations on both transverse faces. In another example, there may be one ridge only, on one of the transverse faces, and one set of serrations only, on the same or the opposed transverse face.

FIG. 8 also shows another feature not found in the embodiment of FIGS. 3-5. A pattern of serrations 100 is formed on at least one of the anterior platforms 56, to provide a gripping action with the cortical bone region of the vertebra. The pattern of serrations 100 can be placed on neither, one, or both of the anterior platforms 56.

Figure 9:
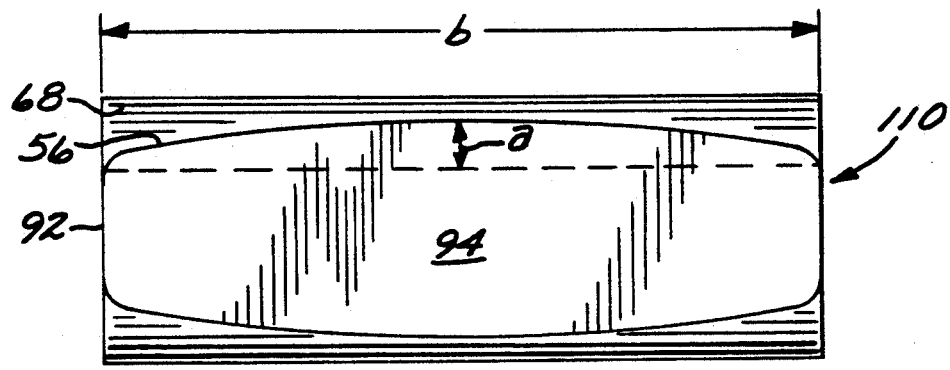
FIG. 9 is an anterior elevational view of another embodiment of the spinal disk implant.
Figure 10:
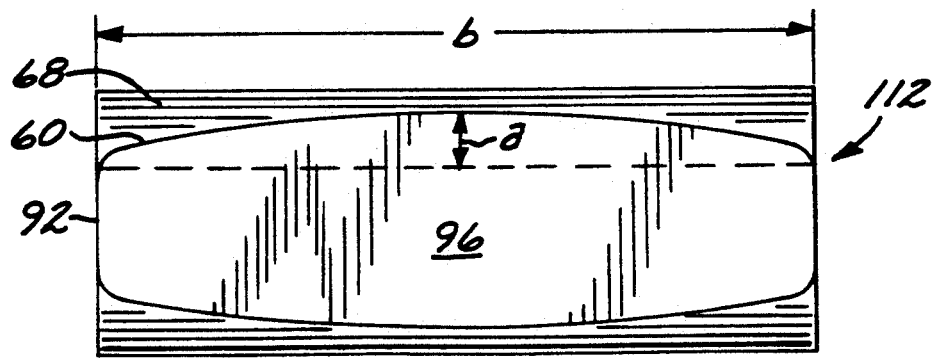
FIG. 10 is a posterior elevational view of another embodiment of the spinal disk implant.
Figure 11:
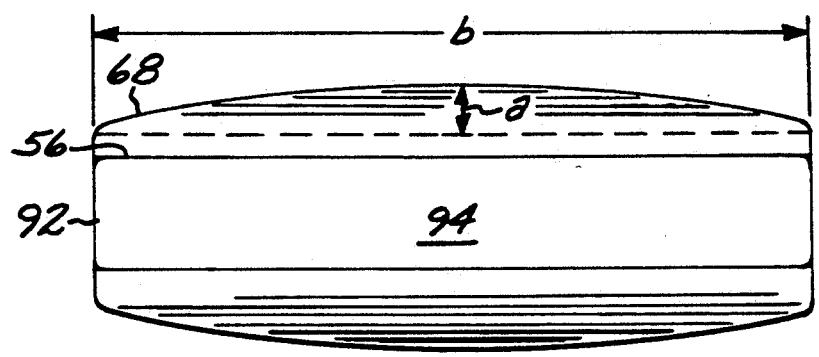
FIG. 11 is an anterior elevational view of another embodiment of the spinal disk implant.

Three other embodiments of the invention are shown in FIGS. 9-11. FIG. 9 is an elevational view from the anterior face side of an implant 110, whose construction is similar to that shown in FIG. 4, except that one or both of the anterior platforms 56 is bowed outwardly (i.e., of convex shape) relative to the body of the implant. FIG. 10 is an elevational view from the posterior face side of an implant 112, whose construction is similar to that shown in FIG. 4, except that one or both of the posterior ledges 60 is bowed outwardly (i.e., of convex shape) relative to the body of the implant. FIG.

11 is an elevational view of an implant 116, except that one or both of the ridges 68 is bowed outwardly (i.e., of convex shape) relative to the body of the implant. The shape of the bowed anterior platform 56, posterior ledge 60, or ridge 68 is not critical. It may be close to an arc of a circle, or not. The corners are typically rounded slightly to reduce stresses. The shape may be conveniently described as the ratio of the height of the bow above the end points, the dimension a in FIGS. 9–11, divided by the distance between the bases 92, the dimension b in FIGS. 9–11. Preferably, for a bowed construction, the degree of bowing as measured by a/b is more than 0 and no greater than about 0.2.

The outward bowing of the anterior platform 56, the posterior ledge 60, or the ridge 68 can be provided to more closely match the available surface of the vertebra, and also reduce concentrated stresses on the surface of the implant that might cause its premature failure. That is, in some instances it may be desirable to form the exposed face of the vertebra to a slightly concave shape, to which the convex shape of the implant conforms more closely.

The various features discussed in relation to the embodiments of FIGS. 3–5 and 8–11 may be used in various combinations for particular requirements and procedures, as long as the limitations of the invention as set forth herein are met.

Returning to a discussion of the preferred implant 50 of FIGS. 3–5 (which is also applicable to the other implants of FIGS. 8–10), the implant 50 is desirably made from a material that, after surgical implantation, bonds to the natural bone of the adjacent vertebrae to form a rigid structure. The implant is preferably made from a ceramic, most preferably the ceramic calcium hydroxylapatite, having a chemical formula $Ca_{10}(PO_4)_6(OH)_2$. The use of such materials in implants is known, see for example U.S. Pat. No. 4,863,476, whose disclosure is incorporated by reference. The implant 50 may also be made from a composite material such as the carbon-fiber reinforced plastics disclosed in U.S. Pat. No. 4,904,261, whose disclosure is incorporated by reference. The implant may also be made from a biocompatible orthopedic polymer ("BOP"), such as a copolymer of methylmethacrylate and N-vinylpyrrolidone and calcium gluconate, reinforced with polyamide fibers. Such a material is known in the art, and is described, for example, in G. Lozes et al., "Discectomies of the Lower Cervical spine Using Interbody Biopolymer (BOP) Implants", *Acta Neurochir (Wien)*, vol. 96, pages 88–93 (1989). In some instances, the implant may be made from an uncoated biocompatible metal, such as titanium or a titanium alloy such as Ti-6Al-4V, or a nonreactive metal such as gold, or such a metal coated with a layer of the ceramic.

Another approach for the construction of the implant is shown in FIG. 5. A coated implant 74 is prepared by providing a piece of metal 76, such as titanium or titanium alloy, in the shape of the implant but slightly undersize in all dimensions. A coating 78 of ceramic or polymer, of the types described previously, is applied over the piece of metal 76 to enlarge the implant 74 to the proper final dimensions.

The implant 50 may be made microporous, so that it functions as a delivery vehicle for antibiotics or bone stimulating factors such as bone morphogenic protein or osteogenin, which are introduced into the implant before implantation surgery. In the case of the preferred ceramic hydroxylapatite construction of the implant, the density and/or surface morphology of the ceramic can be varied in the sintering process so that it retains the materials to be delivered. The delivery of chemicals by this approach is known in the art, see, for example, H. A. Benghuzzi et al., "The Effects of Density of the Ceramic Delivery Devices on Sustained Release of Androgens in Castrated Rodents," 17th Annual Meeting of the Society for Biomaterials, May 1–5, 1991, page 159.

Any of the implants discussed herein is surgically implanted by a technique indicated schematically in FIG. 6. FIG. 6A is a detail of FIG. 1, illustrating two vertebrae 22 and the intervertebral disk 24 between them. In an anterior discectomy, the disk 24 is first removed, FIG. 6B, and the facing surfaces of the vertebrae 22 smoothed. A facing, opposed groove 80 is ground into both the superior vertebra 22a and the inferior vertebra 22b (or only one vertebra if the implant to be used has only one ridge), using a drill 86 with a burr end, FIG. 6C. The groove 80 extends transversely to the vertebrae, in a transverse direction 84 (shown in FIG. 2). The groove 80 is positioned to produce a flush placement of the implant, in the manner to be described in relation to FIG. 6F. The radius of the groove 80 is substantially the same as the radius of the ridge 68, ensuring a close contact between the ridge 68 and the inside of the groove 80.

Figure 6A:
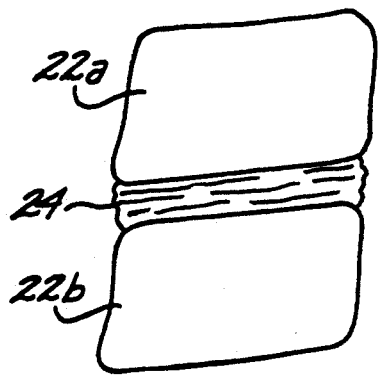
FIG. 6A is a detail of FIG. 1.
Figure 6B:
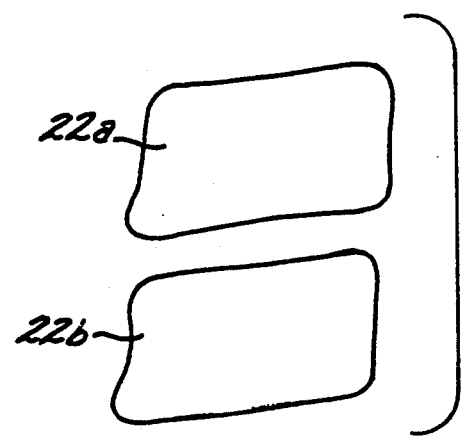
FIG. 6B is the same region as FIG. 6A after removing the natural intervertebral disk.
Figure 6C:
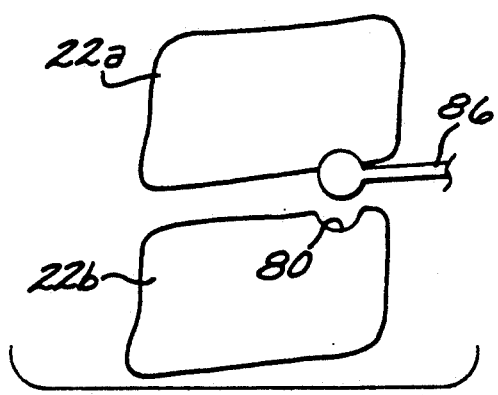
FIG. 6C depicts the formation of a retaining groove in the vertebrae.
Figure 6D:
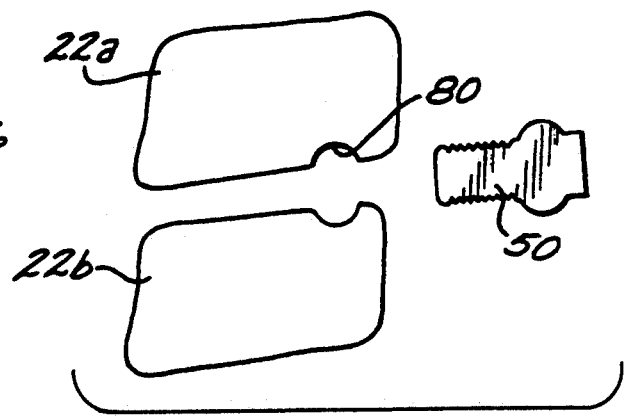
FIG. 6D depicts placement of the spinal implant of FIG. 3.
Figure 6E:
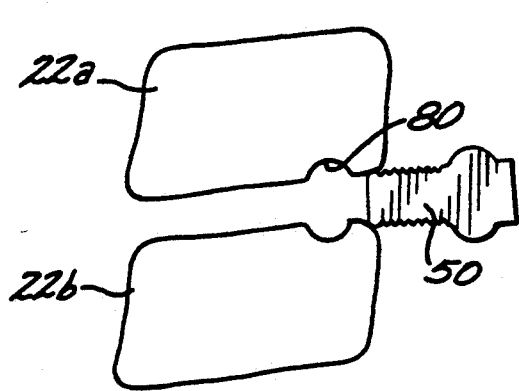
FIG. 6E depicts insertion of the spinal implant.
Figure 6F:
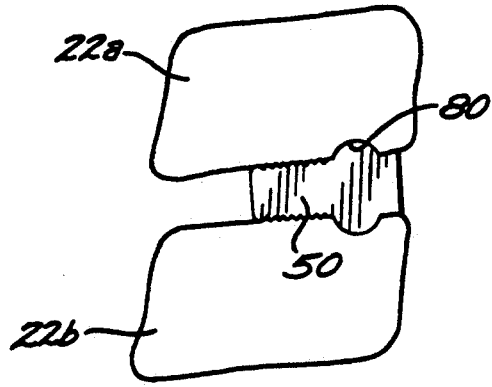
FIG. 6F depicts the implant in place between the vertebrae.

The implant of the geometry discussed herein is selected with the spacing 58 about that of the spacing between the anterior edges 42 of the vertebrae 22. The implant 50 is placed adjacent the vertebrae 22a and 22b, with the tapered end of the posterior ledge 60 inserted between the vertebrae 22a and 22b as shown in FIGS. 6D and 6E. The implant 50 is then tapped with a surgical hammer on the exposed end to drive the implant between the vertebrae. The spine 20 is typically distended slightly during this final stage of insertion to ease the insertion. FIG. 6F illustrates the final placement of the implant 50 or 74 between the vertebrae 22a and 22b.

Figure 7:
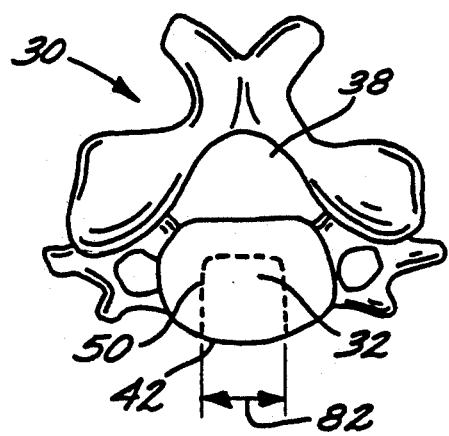
FIG. 7 is a plan view of a cervical vertebra similar to the view of FIG. 2, with the properly positioned spinal disk implant indicated in phantom lines.

FIG. 7 shows a plan view of the implant 50 properly positioned with respect to the vertebra 22. The implant 50 is positioned in the anterior region of the vertebral body 32, well away from the foramen 38 to avoid contact of the implant with the spinal cord. The lateral width 82 of the implant 50 or 74 is less than or equal to that of the vertebral body region 32 of the vertebra 22. The anterior platform 56 is aligned with the anterior edge 42 of the vertebra 22, which is made of hard cortical bone. The primary reaction path for the largest spinal loading is through the anterior edge regions of the vertebrae and the anterior platform 56 of the implant. The ridge 68, posterior ledge 60, and pattern of serrations 66 on the posterior ledge 60 are aligned primarily with the central portion 44 of the vertebra 22, which is made of softer and more resilient cancellous bone. The ridge 68 and the serrations 66 tend to lock the implant 50 or 74 into place and prevent dislocation of the implant, by a keying action. The ridge 68 keys with the groove 80, while the pattern of serrations 66 tends to interlock with the cancellous bone. The serrations also increase the bonding area during subsequent interaction between the natural bone of the vertebra and the implant material.

The present approach provides an implant and process or technique for its use. The implant is of a design and material of construction selected to improve the fusion of the adjacent vertebrae, and to permit the implant to be readily implanted. Although particular embodiments of the invention have been described in detail for purposes of illustration, various modifications may be made without departing from the spirit and scope of the invention. Accordingly, the invention is not to be limited except as by the appended claims.

What is claimed is:

1. A biocompatible spinal disk implant, comprising a solid body having four sides and a pair of spaced-apart, opposed bases, the four sides including spaced-apart, opposed anterior and posterior faces, and
   a pair of spaced-apart, opposed transverse faces, each transverse face having
       an anterior platform directly adjacent to the anterior face, the anterior platform being spaced apart from an opposed anterior platform by a maximum anterior platform spacing, and
       a posterior ledge directly adjacent to the posterior face and being oriented at an insertion angle relative to an opposed posterior ledge of an opposed transverse face, at least one of the posterior ledges having thereon a pattern of serrations; and
   a ridge on at least one of the transverse faces positioned between the anterior platform and the posterior ledge and extending in a direction perpendicular to the bases, a top of the ridge being spaced apart from the opposed transverse face by an amount greater than the anterior platform spacing.

2. The implant of claim 1, wherein the implant is made of a ceramic.

3. The implant of claim 1, wherein the implant is made of ceramic-coated metal.

4. The implant of claim 2, wherein the ceramic is hydroxylapatite.

5. The implant of claim 3, wherein the ceramic is hydroxylapatite.

6. The implant of claim 3, wherein the metal is selected from the group consisting of titanium and a titanium alloy.

7. The implant of claim 1, wherein the implant is made of a material that bonds to natural bone.

8. The implant of claim 1, wherein the implant is made of a microporous material.

9. The implant of claim 1, wherein the ridge is rounded at the top.

10. The implant of claim 1, wherein the insertion angle is from 0 to about 10 degrees.

11. The implant of claim 1, wherein the insertion angle is from 0.5 to about 10 degrees.

12. The implant of claim 1, wherein a surface of the ridge is smooth.

13. The implant of claim 1, wherein a spacing of the posterior ledges at an end adjacent to the ridge is no greater than the spacing of the anterior platforms.

14. The implant of claim 1, wherein the implant is made at least in part of biocompatible orthopedic polymer materials.

15. The implant of claim 1, further including a pattern of serrations on at least one of the anterior platforms, the pattern of serrations extending in a direction perpendicular to the bases.

16. The implant of claim 1, wherein both of the transverse faces have a ridge thereon.

17. A biocompatible spinal disk implant, comprising a solid body having four sides and a pair of spaced-apart, opposed bases, the four sides including spaced-apart, opposed anterior and posterior faces, and
   a pair of spaced-apart, opposed transverse faces, each transverse face having
       an anterior platform directly adjacent to the anterior face, the anterior platform being spaced apart from an opposed anterior platform by a maximum anterior platform spacing, and
       a posterior ledge directly adjacent to the posterior ledge and being oriented at an insertion angle relative to an opposed posterior ledge of an opposed transverse face; and
   a ridge on at least one of the transverse faces positioned between the anterior platform and the posterior ledge and extending in a direction perpendicular to the bases, a top of the ridge being spaced apart from the opposed transverse face by an amount greater than the anterior platform spacing, at least one of the anterior platform, the posterior ledge, and the ridge being bowed outwardly.

18. The implant of claim 17, wherein at least one of the anterior platforms is bowed outwardly when viewed perpendicular to the anterior face.

19. The implant of claim 18, wherein a degree of bowing, as measured by a ratio of a height of a bow to a distance between the bases, is more than 0 and no greater than about 0.2.

20. The implant of claim 17, wherein at least one of the posterior ledges is bowed outwardly when viewed perpendicular to the posterior face.

21. The implant of claim 20, wherein a degree of bowing, as measured by a ratio of a height of a bow to a distance between the bases, is more than 0 and no greater than about 0.2.

22. The implant of claim 17, wherein the ridge is bowed outwardly when viewed perpendicular to the anterior face.

23. The implant of claim 22, wherein a degree of bowing, a measured by a ratio of a height of a bow to a distance between the bases, is more than 0 and no greater than about 0.2.

24. The spinal disk implant of claim 17, wherein at least one of the posterior ledges has a pattern of serrations thereon.

* * * * *